United States Patent [19]

Homan et al.

[11] Patent Number: 4,744,978

[45] Date of Patent: May 17, 1988

[54] HAIR TREATING COMPOSITION CONTAINING CATIONIC ORGANIC POLYMER AND CARBOXYFUNCTIONAL SILICONE

[75] Inventors: Gary R. Homan, Midland; Susan M. Cornwall, Owosso, both of Mich.

[73] Assignee: Dow Corning Corporation, Midland, Mich.

[21] Appl. No.: 791,047

[22] Filed: Oct. 24, 1985

[51] Int. Cl.⁴ .................. A61K 7/06; A61K 7/00; A45D 7/00

[52] U.S. Cl. .......................... 424/70; 424/47; 424/DIG. 1; 424/DIG. 2; 132/7

[58] Field of Search ................ 424/70; 132/7

[56] References Cited

U.S. PATENT DOCUMENTS 4,445,521 5/1984 Grollier et al. ............... 132/7
4,501,619 2/1985 Gee .......................... 106/287.12

FOREIGN PATENT DOCUMENTS 0095238 11/1983 European Pat. Off. .
2114580A 8/1983 United Kingdom .
2123694A 2/1984 United Kingdom .

OTHER PUBLICATIONS 637,992, Cornwall et al., Hair Setting Method Using Aminoalkyl Substituted Polydiorganosiloxane 8/6/84.

Primary Examiner—Albert T. Meyers
Assistant Examiner—F. Krosnick
Attorney, Agent, or Firm—Marc C. Pawl

[57] ABSTRACT

Hair care compositions are disclosed containing a combination of carboxyfunctional polydimethylsiloxane and a cationic, organic polymer. The compositions can be used as hair fixatives and as such may be formulated into aerosol, pump spray, lotion, cream or mousse type hair care products. The compositions are especially effective in providing flexible, long-lasting hold to hair styles.

14 Claims, No Drawings

HAIR TREATING COMPOSITION CONTAINING CATIONIC ORGANIC POLYMER AND CARBOXYFUNCTIONAL SILICONE

BACKGROUND OF THE INVENTION

This invention relates to a composition for treating hair and especially for setting curls in hair. More particularly, the invention relates to the combination of carboxyfunctional silicone and cationic organic polymer components in hair care formulations to provide long-lasting and more durable hair styles.

Many popular hair styles require a means to hold the hair in a desired configuration. Several procedures are commonly used for setting hair styles at home and in beauty salons including, for example, the winding of wetted hair around curlers or rods followed by drying; the winding of moist hair around a hot curling iron; and the blow drying of wet hair while rolling the hair around a hand held brush. It is generally recognized that the physical and chemical action of water plays a significant role in the process of setting hair. When hair is wetted, hydrogen bonds in the keratin of hair are broken. Then when hair is shaped using curlers, irons, or brush and dried, hydrogen bonds are reformed at locations different from the previous ones and the hair style is thus set.

When hair is set by the use of water alone, the hair style gradually loses its shape through the absorption of atmospheric moisture and consequent rearrangement of the hydrogen bonds. A considerable number of hair-setting compositions have been suggested to facilitate the setting of hair styles and especially to extend the time period that the set is retained in the hair. Such compositions range from the permanent wave types which operate chemically by breaking and reforming disulfide linkages in the hair protein to preparations which leave a thin layer of film-forming resin on the hair which when dried tends to mechanically maintain the hair in the shape of the dried resin film. Generally, the film-forming resin preparations have been composed of water or alcohol solutions of anionic polymers such as polyvinylpyrrolidone, polyvinylpyrrolidone-vinylacetate copolymers, polymethacrylate resins, ethyl and butyl monoesters of polymethylvinyl ether and maleic acid, or carboxylated polyvinylacetate copolymers.

While the film-forming resin preparations do improve the length of set retention in hair, it has generally been found that the stiff resin film tends to make the hair objectionably sticky and to produce flaky or linty particles on the hair as the film breaks up during combing or brushing. Moreover, because of the hydrophilic nature of the resins, they are removed from the hair with each shampooing and must be continually reapplied to be effective. The sticky and stiff character of the resin films also makes the coated hair difficult to comb or brush and may result in damaging or breaking hairs during such operations.

On the other hand, organic cationic compounds and polymers such as stearyldimethylbenzylammonium chloride, quaternary nitrogen derivatives of cellulose ethers, and homopolymers and copolymers of dimethyldiallylammonium chloride are well known for use in hair conditioning formulations. Hair conditioners facilitate combing out hair and impart softness and suppleness to the hair. Cationic polymers are further known in the art for their substantivity which enables them to become fixed to hair and to remain on hair. However, in comparison to the anionic polymers, conventional cationics generally show little effect in facilitating the setting of hair styles or providing retention of hair sets over extended periods.

Accordingly, it is a purpose of the present invention to provide improved hair care compositions that are substantive and fixed to hair; facilitate the setting of hair styles; increase the durability of a set in hair; do not make hair feel unnaturally sticky or stiff; and provide flexible hold for hair so that it can be combed after setting without producing objectionable flaky or linty particles.

Starch in European Pat. application No. 95,238 A, teaches that an aqueous emulsion of aminoalkyl substituted polydimethylsiloxane is useful to condition hair because it facilitates combing and imparts a smooth feel to hair. Starch further teaches that polydimethylsiloxanes substituted with other functional groups such as carboxy, thioalkylcarboxy, and quaternary nitrogen would also be useful in the aqueous emulsion to condition hair. This patent application does not teach or suggest using the substituted siloxanes in setting hair or to increase the length of time a set is retained in hair.

Cornwall et al. in U.S. Pat. No. 4,586,518 filing date Aug. 6, 1984 which is assigned to the same assignee as the present application, teach a method of setting hair using a composition containing aminoalkyl substituted polydimethylsiloxane. The presence of the siloxane on the hair is reported to provide both conditioning and set holding. Cornwall et al. further show a hair-setting composition containing a combination of aminoalkyl substituted polydimethylsiloxane and cationic organic resin described as a quaternary nitrogen derivative of cellulose ether.

Grollier et al. in UK Pat. application Nos. 2,123,694 A and 2,114,580 A describe hair-setting compositions containing combinations of cationic polymer and anionic polymer or latex. An aminoalkyl substituted polysiloxane is listed among the many cationic polymers mentioned as useful in the hair-setting compositions.

Gee in U.S. Pat. No. 4,501,619 describes aqueous emulsions of carbonyl-containing silicone fluids and teaches their general utility in textile treatment processes.

SUMMARY OF THE INVENTION

The present invention relates to a composition suitable for treating hair which comprises (A) a carboxyfunctional polysiloxane which conforms generally to the formula

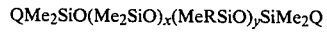

wherein Me denotes the methyl radical, R denotes a carboxyfunctional radical selected from the group consisting of carboxyalkyl radicals, carboxyalkylthio radicals, alkoxycarbonylalkyl radicals, and alkoxycarbonylalkylthio radicals, Q denotes a methyl radical or R, x has an average value from 30 to 400, and y has an average value from 1 to 30, and (B) a cationic, organic polymer containing amine or ammonium groups in the polymer chain or joined to the polymer chain, in a suitable aqueous or organic solvent carrier, wherein the weight ratio of (A) to (B) in the composition is within the range of 0.1 to 5. The present hair treating compositions may be formulated into many types of hair care products such as shampoos, setting lotions or gels, aerosol or pump sprays, mousses and conditioners to facilitate long-lasting hair styling with a flexible, combable hold.

The present invention further relates to a method of setting hair comprising the steps of: rolling the hair around a shaping device, moistening the hair with water, applying to the hair an effective amount of the composition of this invention, and drying the hair while the hair is rolled.

DETAILED DESCRIPTION OF THE INVENTION

The hair-setting compositions of the present invention contain a unique combination of silicone and organic polymer components. When the composition is applied to hair, it forms a film on the hair which holds desired shapes in the hair. The composition is especially advantageous in that it produces a flexible holding-film on hair which allows combing the hair without losing the hold and without forming flaky or linty particles from breakup of the film. Moreover, the holding-film provides retention of hair shapes over extended periods of time even under humid conditions.

The carboxyfunctional polysiloxanes used in the present invention are fluid polymers which are generally described by the average formula

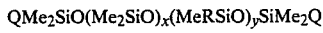

QMe$_2$SiO(Me$_2$SiO)$_x$(MeRSiO)$_y$SiMe$_2$Q wherein Me denotes the methyl radical and Q denotes a methyl radical or R. The average value of x for the polysiloxanes can vary from about 30 to about 400 and the average value of y can vary from about 1 to about 30. More preferably, the average value of x is from 50 to 200 and the average value of y is from 2 to 10. Polysiloxanes within the preferred ranges of polymerization are generally more easily formulated by such means as emulsification in aqueous systems and provide economical yet effective amounts of carboxyfunctional units.

Carboxyfunctional radicals in the polysiloxane are denoted by R and are selected from the group consisting of carboxyalkyl radicals, carboxyalkylthio radicals, alkoxycarbonylalkyl radicals, and alkoxycarbonylalkylthio radicals.

Carboxyalkyl radicals are substituents containing the carboxyl group, —COOH, linked to silicon atoms by a divalent (alkylene) radical such as methylene, ethylene, propylene, trimethylene, tetramethylene, 1-methyltrimethylene, hexamethylene, decamethylene, cyclohexylene and dodecamethylene. Specific examples of carboxyalkyl radicals include carboxymethyl, 2-carboxyethyl, 2-carboxy-2-methylethyl (—CH$_2$CH(CH$_3$)COOH), 5-carboxypentyl, 4-carboxy-2,3-dimethylbutyl, 10-carboxydecyl and the like. The preferred carboxyalkyl radicals for the present invention are 2-carboxyethyl and 2-carboxy-2-methylethyl (—CH$_2$CH(CH$_3$)COOH).

Carboxyalkylthio radicals according to the present invention are substituents containing the carboxyl group, —COOH, linked to silicon atoms by a divalent (alkylene) radical wherein the alkylene radical contains a divalent sulfur atom within the alkylene radical. By "within the alkylene radical" it is meant that the sulfur atom is positioned internally in the alkylene chain and is not located at a terminal position of the radical. Specific examples of carboxyalkylthio radicals include, among others, 4-carboxy-3-thiabutyl (—CH$_2$CH$_2$SCH$_2$COOH), 8-carboxy-7-thiaoctyl, 6-carboxy2-methyl-4-thiahexyl, 6-carboxy-4-thiahexyl, and 4-carboxy2-methyl-3-thiabutyl. The preferred carboxyalkylthio radical for the present invention is 4-carboxy-3-thiabutyl.

Alkoxycarbonylalkyl radicals and alkoxycarbonylalkylthio radicals are substituents containing ester groups, —COOR', linked to silicon atoms by either alkylene radical or sulfurcontaining alkylene radicals as described above. In the ester group, R' denotes an alkyl radical preferably having 1 to 4 carbon atoms such as methyl, ethyl, propyl, or butyl. Preferably, R' in the ester group is methyl. Specific examples of the alkoxycarbonylalkyl radicals and alkoxycarbonylalkylthio radicals include, among others, 4-methoxycarbonyl-3-thiabutyl (—CH$_2$CH$_2$SCH$_2$COOCH$_3$), 4-methoxycarbonyl-2-methyl-3-thiabutyl, 2-ethoxycarbonylethyl, 2-methoxycarbonyl-2-methylethyl, and 6-ethoxycarbonyl-4-thiahexyl.

Generally, it is preferred that the carboxyfunctional radical contain from 3 to 10 carbon atoms and that it is selected from the group consisting of carboxylalkyl radicals and carboxyalkylthio radicals. For example, preferred carboxyfunctional radicals are the 4-carboxy-3-thiabutyl radical, the 2-carboxyethyl radical, the 2-carboxy-2-methylethyl radical, the 8-carboxy-7-thiaoctyl radical, the 6-carboxy-4-thiahexyl radical, and the 6-carboxy-2-methyl-4-thiahexyl radical.

Carboxyfunctional polysiloxanes are known materials, some of which are available commercially and others can be prepared by known processes. For example, silanes or siloxanes containing carboxyfunctional groups can be prepared by reacting appropriate unsaturated carboxyfunctional compounds with silanes or siloxanes containing Si-H functionality. Alternatively, mercaptocarboxylic acids such as mercaptoacetic acid can be added to silanes or polysiloxanes containing alkenyl substituents. The procedures for preparing carboxyfunctional polysiloxanes are further described in U.S. Pat. No. 4,501,619, which is hereby incorporated by reference.

The cationic, organic polymers used in the present invention are well known materials that typically are nonflowing, solid or rubbery solid materials at room temperature. The polymers are characterized primarily as having amine or ammonium groups either in the polymer chain or in substituents joined to the polymer chain. The amine or ammonium groups provide the polymers with their cationic character which is believed to be responsible for their substantivity to hair. The polymers are generally soluble or readily dispersible in water. The cationic organic polymers are described in detail in UK Pat. application 2,114,580 and in U.S. Pat. No. 4,445,521, which is hereby incorporated by reference to further describe and provide examples of the cationic, organic polymers.

Cationic, organic polymers include, among other, quaternary ammonium derivatives of cellulose ethers; copolymers of vinylpyrrolidone and dimethylaminoethylmethacrylate; terpolymers of vinylcaprolactam, vinylpyrrolidone, and dimethylaminoethylmethacrylate; quaternary ammonium derivatives of copolymers of vinylpyrrolidone and dimethylaminoethylmethacrylate; copolymers of acrylamide and dimethyldiallylammonium halide; and quaternary ammonium derivatives of copolymers of acrylamide and dimethylaminoethylmethacrylate.

Although any of the cationic, organic polymers can be used in the compositions of this invention, polymers containing quaternary ammonium groups are preferred. Compositions containing these polymers provide more effective and more durable holding-films when applied to hair. Specific preferred polymers include quaternary ammonium derivatives of cellulose ethers, quaternary ammonium derivatives of copolymers of vinylpyrrolidone and dimethylaminoethylmethacrylate, copolymers of acrylamide and dimethyldiallylammonium halide, and quaternary ammonium derivatives of copolymers of acrylamide and dimethylaminoethylmethacrylate. Among the preferred polymers, the copolymers of acrylamide and dimethyldiallylammonium halide are most preferred.

The combination of cationic, organic polymer and carboxyfunctional silicone is generally diluted in a suitable carrier liquid to facilitate obtaining even and effective treatment of the hair. Any suitable aqueous or organic solvent can be used to dissolve or disperse the active polymer components for this invention. Suitable carrier liquids for hair care formulations are well known in the art and include, among others, water, alcohols such as ethanol or isopropanol, hydrocarbons and halogenated hydrocarbons such as mineral spirits and trichloroethane.

The amount of carrier used in the compositions is not critical and can vary over a wide range. Usually, it is preferred, for ease of application, to use compositions containing from 0.1 to about 20 percent by weight of the combination of polysiloxane and organic polymer. It is even more preferred that the composition contain 0.5 to 8 percent by weight of the combination of polysiloxane and organic polymer.

The hair-treating compositions can be prepared by dissolving the polysiloxane and organic polymer in a physiologically acceptable organic solvent. Alternatively, hair-treating compositions can be prepared by forming an aqueous dispersion, emulsion, or microemulsion of the polysiloxane in an aqueous solution of the organic polymer. The polysiloxane may be emulsified in an aqueous solution of organic polymer or the polysiloxane may be first emulsified in water and then the polysiloxane emulsion combined with an organic polymer solution. Aqueous dispersions, emulsions, or microemulsions of polysiloxane may be prepared by mixing the polysiloxane in water using emulsifying agents as is well known in the art. For example, the emulsification of carboxyfunctional polysiloxanes is described in U.S. Pat. No. 4,501,619. When dispersing or emulsifing the polysiloxane in water, it is preferred to employ an effective amount of a nonionic surfactant. Nonionic surfactants are well known in the hair care art and need not be further described here.

The weight ratio of polysiloxane to organic polymer in the compositions of the present invention is within the ratio of about 0.1 to 5 inclusive. For example, the composition may contain 10 parts polysiloxane and 90 parts organic polymer, 50 parts polysiloxane and 50 parts organic polymer, or 80 parts polysiloxane and 20 parts organic polymer. It is even more preferred to use compositions wherein the ratio of polysiloxane to organic polymer is in the range of 0.2 to 3 inclusive. Compositions with the above ratio of components are preferred because they generally provide a very desirable combination of flexible fixation and conditioning effects on hair.

The compositions of this invention provide many improvements in hair characteristics that are not obtained by the use of either polysiloxane or organic polymer alone. For example, on wet hair, the composition improves the ease of wet combing and provides a silkier touch. Once the treatment is dried, a film is formed on individual hair strands which mechanically holds the shape of the hair, but the hair continues to exhibit silkier touch and easy combing characteristics. While the organic polymer alone may provide some silkiness and improved combing, the combination with polysiloxane enhances these properties. Typically, the organic polymer alone has a tacky feel which is detackified upon addition of the polysiloxane. Similarly, while the organic polymer alone on hair may provide some set-holding effect, the combination of polysiloxane and organic polymer on hair provides better set-holding because the set is more durable, long-lasting, flexible, and lubricated for improved combing ease.

The compositions of this invention may also contain other components such as surfactants, thickeners, perfumes, colorants, propellant gases and small amounts of acids or bases to adjust pH as desired. When the composition is intended to be applied to the hair by first placing a portion in the hand and then transferring to the hair, it is preferred that the composition contain a thickener. The concentration of thickeners when used is generally from 0.5 to 30 percent, and preferably from 0.5 to 15 percent by weight.

Thickeners which can be used include sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose and starch amylose and locust bean gum. In nonaqueous carrier systems, hydrophobic thickeners such as polyvinylether and polyvinylisobutyl ether can be used.

Perfumes which can be used in the compositions are the cosmetically acceptable perfumes and they may be present in amounts which vary from 0.1 to 0.5 percent by weight.

When the composition is intended for aerosol application, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane.

The present invention further relates to a method of setting hair comprising the steps of: rolling the hair around a shaping device, moistening the hair with water, applying to the hair an effective amount of the composition of this invention, and drying the hair while the hair is rolled. The steps of the method of this invention may be performed in any order or simultaneously with the only exception being that the hair is dried while the hair is rolled and, of course, after the hair has been moistened with water.

In the method of this invention, a desired shape or configuration is imposed on the hair by rolling the hair around a shaping device. Any of the conventional devices commonly used for setting hair styles may be employed in the method of this invention. For example the hair may be rolled on curlers, a curling iron or a hand held brush. The hair may be rolled while wet such as after shampooing or it may be rolled while dry and then moistened with water. Moistening of dry rolled hair may also be accomplished simultaneously with the application of the treatment composition when the composition of this invention is applied in the form of an aqueous emulsion.

In the method of this invention, the composition may be applied to the surface of the hair in any suitable manner such as by massaging the composition throughout the hair by hand, by dipping the hair into the composition, by brushing or combing the composition through the hair, by spraying the hair, or by padding the hair with sponges or cloth containing absorbed treating composition. The composition may be applied either before the hair is rolled or after it is rolled. Generally, however, it is preferred to apply the composition prior to rolling the hair since it is easier to treat the hair evenly at this stage.

After the composition is applied, the hair may or may not be rinsed with water. However, in a preferred embodiment of the invention, the treating composition is formulated as a hair-setting composition which is intended to be applied to the hair without subsequent water rinsing. Such leave-on compositions of this invention are preferred because they provide more improved and more long-lasting shape holding properties to hair.

Generally the amount of composition is applied that is effective to provide an improvement in curl retention. The amount required will vary with the quantity and type of hair of each individual. Also the amount applied will vary depending on the extent of curl retention desired. Appropriate amounts for any individual's hair are readily determined by one or two trial applications.

The hair is dried while it is rolled in the desired shape or configuration. The hair may be dried by any convenient method such as by heating the hair with a blow dryer, with hot curlers, or with a heated curling iron. The hair may also be allowed to dry naturally at room temperature.

The following examples are presented to illustrate the invention to those skilled in the art and should not be construed as limiting the invention, which is properly delineated in the appended claims. All proportions by parts or percents are by weight unless otherwise stated.

EXAMPLE 1

This example compares the curl durability of hair which has been set after a treatment with either the cationic organic polymer by itself or with a combination of cationic organic polymer and carboxyfunctional polysiloxane.

Dark brown European hair tresses were prepared in two gram bundles with a length of seven inches and hydrated by soaking for two minutes in a three weight percent aqueous non-conditioning shampoo solution followed by a one minute rinse under running water. Hair tresses were treated by massaging 0.6 g of the treatment composition into the hair for 30 seconds and then combing to evaluate detangling, wet feel, and wet comb. After combing, each tress was individually rolled onto a 11/16 inch O.D. curler and allowed to dry overnight at ambient conditions. The hair was then dried in a 60° C. oven for 30 minutes and allowed to cool for 15 minutes before unrolling from the curlers. Each tress was combed through twice and allowed to hang freely under ambient conditions (48-55% RH and 70° F). The initial length of each tress was measured and the tresses were evaluated (on a scale of 1 to 5 with lower numbers indicating preferred characteristics) for dry appearance, dry feel, dry comb, extent of powdering, and body.

After 2 hours and 6 hours, the tress lengths were measured again to determine curl durability. In order to obtain statistically significant results, three tresses were used as an untreated control and six tresses were treated with each test composition. Lengths of tresses for each treatment were averaged and the variation calculated for a 90% confidence level.

Hair tresses were treated by two different compositions. Composition I was a 5 wt. % solids solution in water of dimethyldiallylammonium chloride/acrylamide copolymer which is commercially available as Merquat ® S from Merck & Co, Rahway, N.J.

Composition II was a mixture containing 2.5 wt. % solids of the dimethyldiallylammonium chloride/acrylamide copolymer and 2.5 wt. % of a carboxyfunctional polysiloxane. Composition II was prepared by mixing 61.62 parts of water, 31.25 parts (as supplied at 8 wt. % solids) of Merquat ® S, and 7.13 parts of an emulsion of the polysiloxane. The polysiloxane emulsion contained 35 parts of polysiloxane, 1 part of ethylene glycol, 1 part of octylphenoxypolyethyleneoxide with an average of 9 ethylene oxide units per molecule, 3.6 parts of octylphenoxypolyethyleneoxide with an average of 40 ethylene oxide units per molecule, and 59.4 parts water. The polysiloxane was composed of about 3 mole % $HOOCCH_2SCH_2CH_2(CH_3)SiO$ units, about 95 mole % dimethylsiloxane units, and about 2 mole % of trimethylsiloxane units and had a viscosity of about 250 cs at 25° C.

The hair lengths along with some of the wet and dry properties of the tresses are presented in Table 1. The variation calculated at the 90% confidence level was 0.32 inch for the untreated control tresses and 0.23 inch for the treated tresses. The data indicates that, even after 6 hours, treatment with the organic polymer of Composition I provides about 13.5% reduction in curl length but, surprisingly, treatment with the combined organic polymer-polysiloxane mixture of Composition II provides twice as much (25%) reduction in curl length compared to the control tresses.

TABLE 1

| Property | Treatment | | |
|---|---|---|---|
| | None | I | II |
| Wet Feel | 4 | 3 | 1.5 |
| Wet Comb | 3 | 2 | 1 |
| Wet Tack | 1 | 4.5 | 3 |
| Dry Comb | 2 | 2 | 1 |
| Detangling | 5 | 4 | 2 |
| 2 Hr. Curl Length (inches) | 3.42 | 2.65 | 2.19 |
| 6 Hr. Curl Length (inches) | 3.94 | 3.41 | 2.88 |

EXAMPLE 2

This example further illustrates the improved curl durability provided by the compositions of this invention.

Hair tresses were prepared, treated with Composition III or IV, and rolled on curlers as described in Example 1. The tresses were dried in a 70° C. air-circulating oven for 1 hour and left overnight at ambient conditions before unrolling. Each tress was combed through twice and allowed to hang freely under ambient conditions (40-45% RH and 70° F.). The tress lengths were measured at various times to determine curl durability.

Six tresses were treated with Composition III, a mixture of 2.5 wt. % solids of the quaternary nitrogen derivative of cellulose ether having a viscosity at 25° C. of 125 cp as 2% by weight aqueous solution (commercially available as JR Resin ® 125 from Union Carbide Corporation, New York, N.Y.) and 2.5 wt. of a carboxyfunctional polysiloxane. Composition III was prepared by mixing 90.4 parts of water, 2.5 parts (as supplied at 100 wt. % solids) of JR Resin ® 125, and 7.1 parts of the emulsion of polysiloxane described in Example 1.

Six tresses were treated with Composition IV, a mixture of 2.5 wt. % solids of JR Resin ® 125 and 2.5 wt. % of a carboxyfunctional polysiloxane. Composition IV was prepared by mixing 89.2 parts of water, 2.5 parts (as supplied at 100 wt. % solids) of JR Resin ® 125, and 8.3 parts of an emulsion of polysiloxane. The polysiloxane emulsion used in Composition IV contained 30 parts of polysiloxane, 3 parts of trimethylnonylpolyethyleneoxide with an average of 6 ethylene oxide units per molecule, and 67 parts water. The polysiloxane in this emulsion was composed of about 3 mole % $HOOCCH(CH_3)CH_2(CH_3)SiO$ units, about 95 mole % dimethylsiloxane units, and about 2 mole % of trimethylsiloxane units and had a viscosity of about 340 cs at 25° C.

The hair lengths along with some of the wet properties of the tresses are presented in Table 2. The variation calculated at the 90% confidence level was 0.30 inch for the untreated control tresses and for the treated tresses measured after 2.5 hours and 0.24 inch for the treated tresses measured after 4.5 hours. The data indicates that a significant improvement in curl durability was provided by the compositions of this invention.

TABLE 2

| Property | Treatment | | |
|---|---|---|---|
| | None | III | IV |
| Wet Feel | 3 | 1 | 1.5 |
| Wet Comb | 3.5 | 1.5 | 1 |
| 2.5 Hr. Curl Length (inches) | 2.56 | 1.60 | 1.69 |
| 4.5 Hr. Curl Length (inches) | 2.69 | 1.60 | 1.73 |

EXAMPLE 3

This example illustrates the improved curl durability and other characteristics provided by compositions containing polysiloxanes having alkoxycarbonylalkylthio substituents.

Hair tresses were prepared, treated with Composition V, VI, or VII, and rolled on curlers as described in Example 1. The tresses were allowed to dry overnight at ambient conditions and then further dried in a 60° C. air-circulating oven for 0.5 hour. After cooling for 0.5 hour, each tress was unrolled, combed through twice and allowed to hang freely under controlled conditions (70% RH and 72.5° F.). The tress lengths were measured after 10, 30, and 60 minutes to determine curl durability.

Six tresses were treated with Composition V, a mixture of 2.5 wt. % solids of Merquat ® S and 2.5 wt. % of a carboxyfunctional polysiloxane. Composition V was prepared by mixing 43.7 parts of water, 31.3 parts (as supplied at 8 wt. % solids) of Merquat ® S, and 25 parts of a dispersion of polysiloxane. The polysiloxane dispersion contained 10 parts of polysiloxane, 0.15 part of octylphenoxypolyethyleneoxide with an average of 9 ethylene oxide units per molecule, and 89.85 parts water. The polysiloxane was composed of about 3 mole % $CH_3OOCCH_2SCH_2CH_2(CH_3)SiO$ units, about 95 mole % dimethylsiloxane units, and about 2 mole % of trimethylsiloxane units.

Six tresses were treated with Composition VI, a mixture of 3.35 wt. % solids of Merquat ® S and 1.65 wt. % of a carboxyfunctional polysiloxane. Composition VI was prepared by mixing 40.6 parts of water, 46.9 parts (as supplied at 8 wt. % solids) of Merquat ® S, and 12.5 parts of an emulsion of polysiloxane similar to that described above except that the polysiloxane was composed of about 2 mole % $CH_3OOCCH_2SCH_2CH_2(CH_3)SiO$ units, about 96.7 mole % dimethylsiloxane units, and about 1.3 mole % of trimethylsiloxane units.

Six tresses were treated with Composition VII, a mixture of 1.65 wt. % solids of Merquat ® S and 3.35 wt. % of a carboxyfunctional polysiloxane. Composition VII was prepared by mixing 46.8 parts of water, 15.7 parts (as supplied at 8 wt. % solids) of Merquat ® S, and 37.5 parts of an emulsion of polysiloxane similar to that described above except that the polysiloxane was composed of about 1 mole % $CH_3OOCCH_2SCH_2CH_2(CH_3)SiO$ units, about 97 mole % dimethylsiloxane units, and about 2 mole % of trimethylsiloxane units.

The hair lengths along with some of the wet properties of the tresses are presented in Table 3. The variation calculated at the 90% confidence level ranged from 0.21 inch to 0.16 inch. The data indicates that significant improvements in curl durability and other characteristics were provided by the compositions.

TABLE 3

| Property | Treatment | | | |
|---|---|---|---|---|
| | None | V | VI | VII |
| Wet Feel | 3 | 2 | 3 | 1.5 |
| Wet Comb | 3 | 1.5 | 3 | 1.5 |
| Detangling | 5 | 1.5 | 2 | 2 |
| 10 Min. Curl Length (inches) | 3.25 | 2.73 | 2.84 | 2.78 |
| 30 Min. Curl Length (inches) | 3.83 | 3.23 | 3.24 | 3.44 |
| 60 Min. Curl Length (inches) | 4.11 | 3.44 | 3.44 | 3.64 |

EXAMPLE 4

This example presents compositions of the present invention containing several different examples of cationic, organic polymers with amine or ammonium functionality.

Hair tresses were treated with combinations of organic resin and the emulsion of polysiloxane described in Example 1. Each test composition contained 5 wt. % of combined silicone and organic resin in a water carrier. Each tress was treated, curled, dried, unrolled, and combed twice as described in Example 1. The tresses were allowed to hang freely under ambient conditions (44-60% RH and 70° F.) and the length of each tress was measured after 2, 4, and 6 hours.

The following cationic, organic polymers were used in the compositions:

Polymer 1: A copolymer derivative of hydroxyethyl cellulose with diallyldimethyl ammonium chloride which is commercially available under the name Celquat ® H100 from National Starch & Chemical Corp., Bridgewater, N.J.

Polymer 2: A copolymer of vinylpyrrolidone and dimethylaminoethylmethacrylate which is commercially available under the name GAF Copolymer ® 958 from GAF Corp., Wayne, N.J.

Polymer 3: A terpolymer of vinylcaprolactam, vinylpyrrolidone, and dimethylaminoethylmethacrylate which is commercially available under the name Gaffix ® from GAF Corp., Wayne, N.J.

Polymer 4: A copolymer of vinylpyrrolidone and dimethylaminoethylmethacrylate derivitized with dimethylsulfate to form quaternary ammonium groups pendent from the polymer chain, which is commercially available under the name Gafquat ® 755N from GAF Corp., Wayne, N.J.

Polymer 5: A cationic derivative of starch as described generally in French Pat. application 2,434,821, which is commercially available under the name Lab ® 358 from Roquette Freres SA., France.

Polymer 6: A copolymer of acrylamide and betamethacryloxyethyltrimethyl ammonium methosulfate which is commercially available under the name Reten ® 220 from Hercules, Inc., Wilmington, Del.

Curl lengths for the treated tresses and typical lengths for untreated tresses are presented in Table 4. The lengths shown are averages from three tresses.

TABLE 4

| Copolymer | Weight Ratio Silicone to Copolymer in Treatment | Curl Length (inches) | | |
|---|---|---|---|---|
| | | 2 Hr. | 4 Hr. | 6 Hr. |
| Untreated Hair | — | 3.5 | 3.75 | 4.0 |
| 1 | 1:3 | 2.0 | 2.8 | 3.1 |
| 2 | 1:3 | 2.6 | 2.8 | 3.0 |
| 3 | 1:3 | 2.9 | 3.1 | 3.2 |
| 4 | 1:3 | 2.3 | 2.5 | 2.5 |
| 5 | 1:3 | 2.0 | 2.1 | 2.1 |
| 6 | 1:3 | 2.5 | 2.9 | 3.1 |

That which is claimed is:

1. A method of setting hair comprising the steps of: rolling the hair around a shaping device, moistening the hair with water, applying to the hair without subsequent water rinsing an effective amount of a composition comprising (A) a carboxyfunctional polysiloxane of the formula $$QMe_2SiO(Me_2SiO)_x(MeRSiO)_ySiMe_2Q$$

wherein Me denotes the methyl radical, R denotes a carboxyfunctional radical selected from the group consisting of carboxyalkyl radicals, carboxyalkylthio radicals, alkoxycarbonylalkyl radicals, and alkoxycarbonylalkylthio radicals, Q denotes a methyl radical or R, x has an average value from 30 to 400, and y has an average value from 1 to 30, and (B) a cationic, organic polymer containing amine or ammonium groups in the polymer chain or joined to the polymer chain, in a suitable aqueous or organic solvent carrier, wherein the weight ratio of (A) to (B) in the composition is within the range of 0.1 to 5, and drying the hair while the hair is rolled.

2. A method of setting hair as claimed in claim 1, where in said cationic, organic polymer is selected from the group consisting of quaternary ammonium derivatives of cellulose ethers; copolymers of vinylpyrrolidone and dimethyl-aminoethylmethacrylate; terpolymers of vinylcaprolactam, vinylpyrrolidone and dimethylaminoethylmethacrylate; quaternary ammonium derivatives of copolymers of vinylpyrrolidone and dimethylaminoethylmethacrylate; copolymers of acrylamide and dimethyldiallylammonium halide; and quaternary ammonium derivatives of copolymers of acrylamide and dimethylaminoethylmethacrylate.

3. A method of setting hair as claimed in claim 1, wherein said cationic organic polymer contains quaternary ammonium groups.

4. A method of setting hair as claimed in claim 3, wherein said cationic organic polymer is selected from the group consisting of quaternary ammonium derivatives of cellulose ethers, quaternary ammonium derivatives of copolymers of vinylpyrrolidone and dimethylaminoethylmethacrylate, copolymers of acrylamide and dimethyldiallylammonium halide, and quaternary ammonium derivatives of copolymers of acrylamide and dimethylaminoethylmethacrylate.

5. A method of setting hair as claimed in claim 4, wherein Q denotes the methyl radical, x has an average value of 50 to 200, and y has an average value of 2 to 10.

6. A method of setting hair as claimed in claim 5, wherein said carboxyfunctional radical contains from 3 to 10 carbon atoms.

7. A method of setting hair as claimed in claim 6, wherein said carboxyfunctional radical is selected from the group consisting of carboxyalkyl radicals and carboxyalkylthio radicals.

8. A method of setting hair as claimed in claim 7, wherein said carboxyfunctional radical is selected from the group consisting of the 4-carboxy-3-thiabutyl radical, the 2-carboxyethyl radical, the 2-carboxy-2-methylethyl radical, the 8-carboxy-7-thiaoctyl radical, the 6-carboxy-4-thiahexyl radical, and the 6-carboxy-2-methyl-4-thiahexyl radical.

9. A method of setting hair as claimed in claim 8, wherein the ratio of (A) to (B) in the composition is within the range of 0.2 to 3.

10. A method of setting hair as claimed in claim 9, wherein said carboxyfunctional radical is the 2-carboxy-2-methyethyl radical.

11. A method of setting hair as claimed in claim 9, wherein said carboxyfunctional radical is the 4-carboxy-3-thiabutyl radical.

12. A method of setting hair as claimed in claim 11, wherein said composition contains 0.1 to 20 percent by weight of the combination of (A) and (B).

13. A method of setting hair as claimed in claim 12, wherein said carrier comprises water and the carboxyfunctional polysiloxane is dispersed in water with an effective amount of a nonionic surfactant.

14. A method of setting hair as claimed in claim 13, wherein said composition contains 0.5 to 8 percent by weight of the combination of (A) and (B).

* * * * *